(12) United States Patent
Keith et al.

(10) Patent No.: US 10,842,972 B2
(45) Date of Patent: Nov. 24, 2020

(54) METHODS AND DEVICES FOR PARANASAL SINUS DELIVERY

(71) Applicant: ENTELLUS MEDICAL, INC., Plymouth, MN (US)

(72) Inventors: Peter T. Keith, Lanesboro, MN (US); Reuben C. Setliff, III, Sioux Falls, SD (US)

(73) Assignee: Entellus Medical, Inc., Maple Grove, MN (US)

( * ) Notice: Subject to any disclaimer, the term of this patent is extended or adjusted under 35 U.S.C. 154(b) by 0 days.

(21) Appl. No.: 16/019,356

(22) Filed: Jun. 26, 2018

(65) Prior Publication Data

US 2018/0304051 A1 Oct. 25, 2018

Related U.S. Application Data

(63) Continuation of application No. 15/140,474, filed on Apr. 28, 2016, now Pat. No. 10,029,069, which is a continuation of application No. 12/766,586, filed on Apr. 23, 2010, now Pat. No. 9,333,327.

(60) Provisional application No. 61/172,426, filed on Apr. 24, 2009.

(51) Int. Cl.
| | |
|---|---|
| *A61M 25/10* | (2013.01) |
| *A61B 17/24* | (2006.01) |
| *A61M 27/00* | (2006.01) |
| *A61M 25/00* | (2006.01) |
| *A61F 2/18* | (2006.01) |

(52) U.S. Cl.
CPC ......... *A61M 25/1002* (2013.01); *A61B 17/24* (2013.01); *A61M 25/0012* (2013.01); *A61M 27/002* (2013.01); *A61F 2/186* (2013.01); *A61F 2250/0059* (2013.01); *A61F 2250/0068* (2013.01); *A61M 2025/1004* (2013.01); *A61M 2025/1054* (2013.01); *A61M 2210/0681* (2013.01)

(58) Field of Classification Search
CPC .......... A61M 25/1002; A61M 25/0012; A61M 27/002; A61M 2025/1004; A61M 2025/1054; A61M 2210/0681; A61B 17/24; A61F 2/186; A61F 2250/0059; A61F 2250/0068
See application file for complete search history.

(56) References Cited

U.S. PATENT DOCUMENTS

| | | | |
|---|---|---|---|
| 5,611,775 A | 3/1997 | Machold | |
| 6,543,452 B1 | 4/2003 | Lavigne | |
| 7,410,480 B2 * | 8/2008 | Muni | A61B 5/411 |
| | | | 604/509 |
| 7,419,497 B2 * | 9/2008 | Muni | A61B 17/24 |
| | | | 424/434 |
| 7,520,876 B2 | 4/2009 | Ressemann et al. | |
| 7,678,099 B2 | 3/2010 | Ressemann et al. | |
| 7,842,062 B2 | 11/2010 | Keith et al. | |
| 7,879,061 B2 | 2/2011 | Keith et al. | |
| 7,918,871 B2 | 4/2011 | Truitt et al. | |

(Continued)

*Primary Examiner* — Lauren P Farrar
(74) *Attorney, Agent, or Firm* — McDonnell Boehnen Hulbert & Berghoff LLP

(57) ABSTRACT

Described herein are methods and devices for delivering a drug to the frontal sinus system. An inflatable implant is positioned within the frontal sinus system using an anchoring means secured within the frontal sinus cavity. A drug-containing fluid is released directly into the frontal sinus drainage system.

17 Claims, 6 Drawing Sheets

(56) References Cited

U.S. PATENT DOCUMENTS

| | | |
|---|---|---|
| 8,241,266 B2 | 8/2012 | Keith et al. |
| 8,277,478 B2 | 10/2012 | Drontle et al. |
| 8,282,667 B2 | 10/2012 | Drontle et al. |
| 8,348,969 B2 | 1/2013 | Keith et al. |
| 8,568,439 B2 | 10/2013 | Keith et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,657,846 B2 | 2/2014 | Keith et al. |
| 8,801,670 B2 | 8/2014 | Drontle et al. |
| 8,834,513 B2 | 9/2014 | Hanson et al. |
| 8,882,795 B2 | 11/2014 | Drontle et al. |
| 8,888,686 B2 | 11/2014 | Drontle et al. |
| 8,915,938 B2 | 12/2014 | Keith et al. |
| 8,986,340 B2 | 3/2015 | Drontle et al. |
| 9,005,284 B2 | 4/2015 | Ressemann |
| 9,101,739 B2 | 8/2015 | Lesch, Jr. et al. |
| 9,192,748 B2 | 11/2015 | Ressemann et al. |
| 9,278,199 B2 | 3/2016 | Keith et al. |
| 9,282,986 B2 | 3/2016 | Hanson et al. |
| 9,283,360 B2 | 3/2016 | Lesch et al. |
| 9,320,876 B2 | 4/2016 | Ressemann et al. |
| 9,333,327 B2 | 5/2016 | Setliff, III et al. |
| 9,339,637 B2 | 5/2016 | Drontle et al. |
| 9,370,650 B2 | 6/2016 | Hanson et al. |
| 9,433,343 B2 | 9/2016 | Drontle et al. |
| 9,440,049 B2 | 9/2016 | Drontle et al. |
| 9,486,614 B2 | 11/2016 | Drontle et al. |
| 9,550,049 B2 | 1/2017 | Hanson et al. |
| 9,694,167 B2 | 7/2017 | Keith et al. |
| 9,700,705 B2 | 7/2017 | Lesch, Jr. et al. |
| 9,775,975 B2 | 10/2017 | Ressemann et al. |
| 10,022,525 B2 | 7/2018 | Hanson et al. |
| 10,029,069 B2 | 7/2018 | Keith et al. |
| 10,086,181 B2 | 10/2018 | Lesch |
| 2001/0047163 A1* | 11/2001 | Samson ............... A61M 25/10 604/509 |
| 2008/0015540 A1* | 1/2008 | Muni ............... A61B 17/3421 604/500 |
| 2008/0172033 A1 | 7/2008 | Keith et al. |
| 2009/0171301 A1 | 7/2009 | Becker |
| 2009/0187258 A1 | 7/2009 | Ip |
| 2009/0198216 A1* | 8/2009 | Muni ............... A61M 25/0662 604/514 |
| 2012/0283625 A1 | 11/2012 | Keith et al. |
| 2013/0030458 A1 | 1/2013 | Dontle et al. |
| 2013/0072958 A1 | 3/2013 | Ressemann et al. |
| 2013/0123833 A1 | 5/2013 | Lesch et al. |
| 2014/0350520 A1 | 11/2014 | Drontle et al. |
| 2014/0357959 A1 | 12/2014 | Hanson et al. |
| 2014/0364700 A1 | 12/2014 | Hanson et al. |
| 2014/0378776 A1 | 12/2014 | Hanson et al. |
| 2015/0031950 A1 | 1/2015 | Drontle et al. |
| 2015/0045827 A1 | 2/2015 | Drontle et al. |
| 2015/0105818 A1 | 4/2015 | Keith et al. |
| 2016/0151614 A1 | 6/2016 | Ressemann et al. |
| 2016/0166814 A1 | 6/2016 | Lesch et al. |
| 2016/0367286 A1 | 12/2016 | Drontle et al. |
| 2017/0007282 A1 | 1/2017 | Drontle |
| 2017/0028112 A1 | 2/2017 | Drontle et al. |
| 2017/0050001 A1 | 2/2017 | Drontle et al. |
| 2017/0113027 A1 | 4/2017 | Drontle et al. |
| 2017/0368319 A1 | 12/2017 | Lesch et al. |
| 2018/0008806 A1 | 1/2018 | Ressemann et al. |
| 2018/0304058 A1 | 10/2018 | Hanson et al. |

* cited by examiner

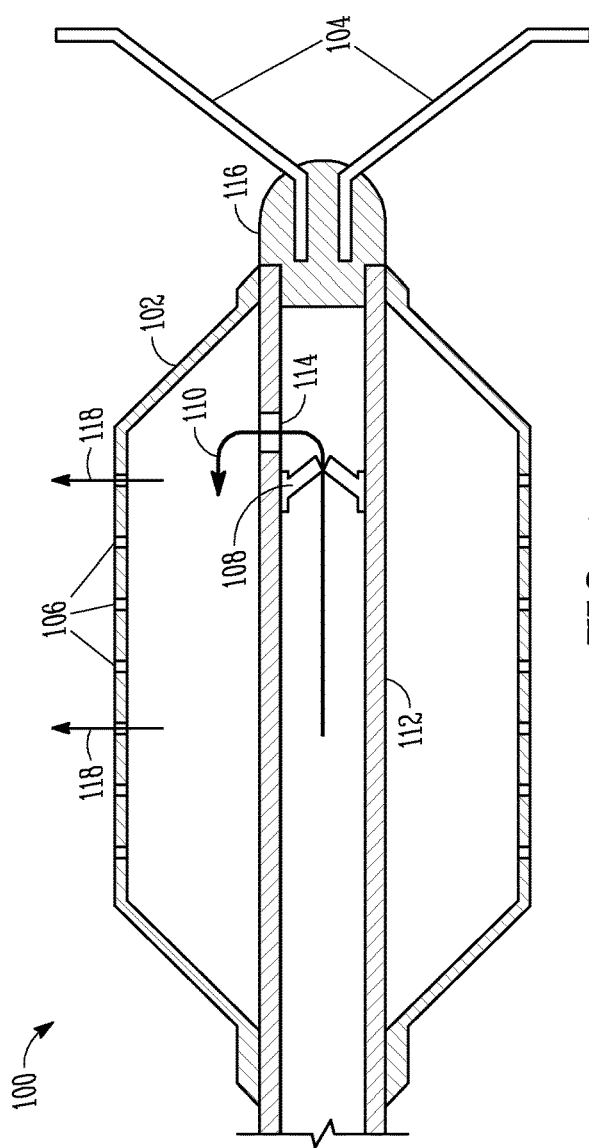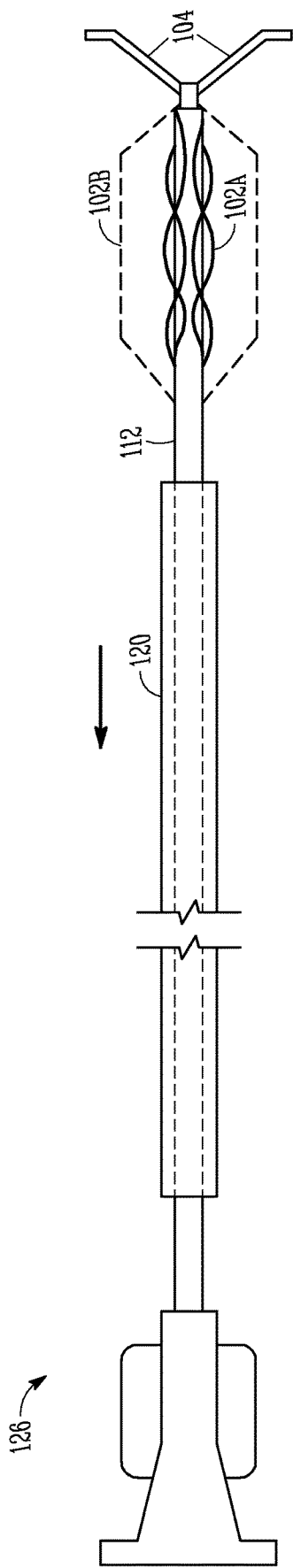
FIG. 1
FIG. 2

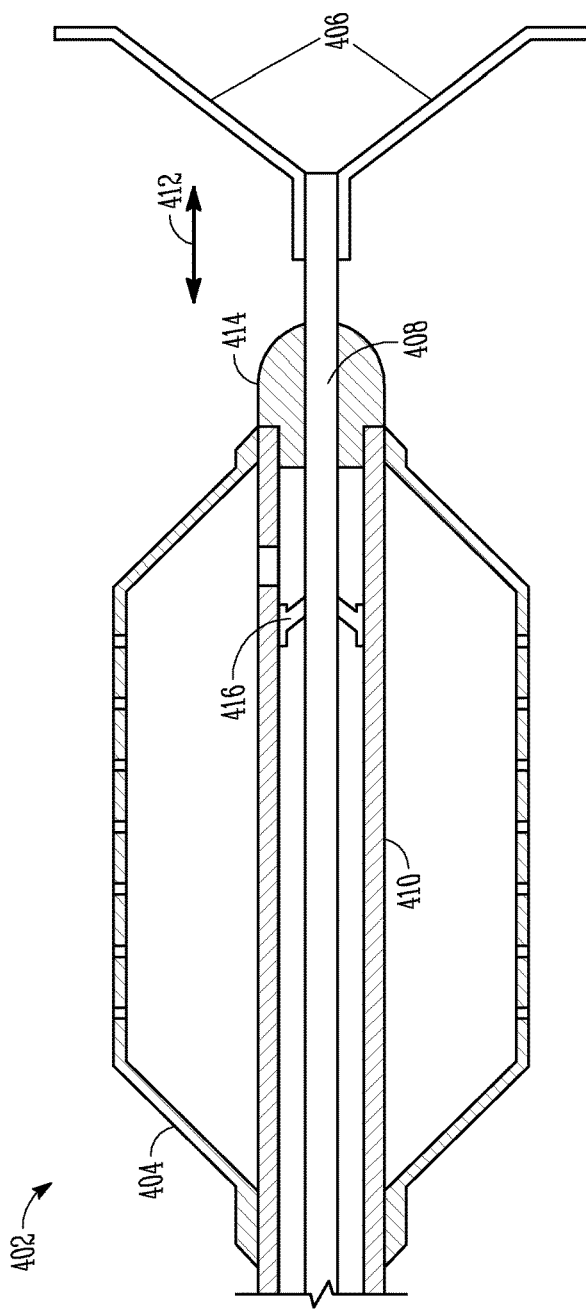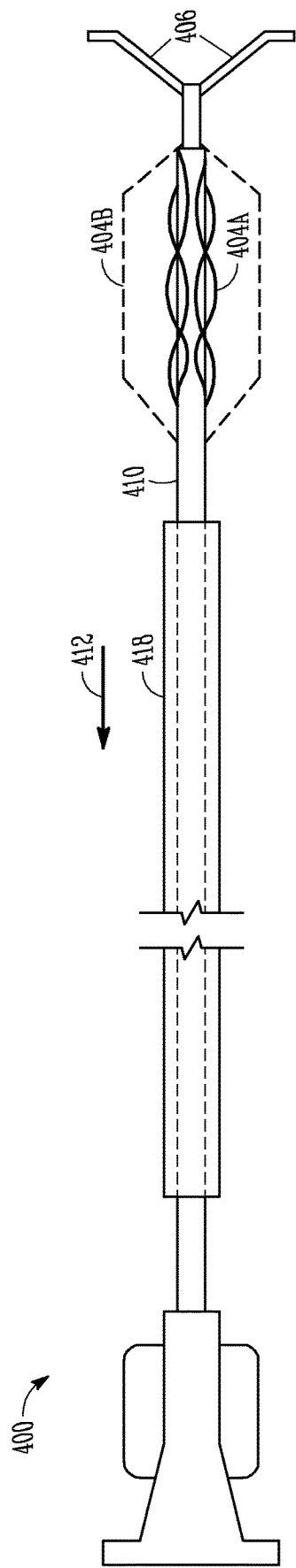
FIG. 4
FIG. 5

METHODS AND DEVICES FOR PARANASAL SINUS DELIVERY

RELATED APPLICATIONS

This Application is a continuation of U.S. application Ser. No. 15/140,474, filed on Apr. 28, 2016, now allowed, which is a continuation of U.S. patent application Ser. No. 12/766,586, filed on Apr. 23, 2010, now issued as U.S. Pat. No. 9,333,327, and claims priority to U.S. Provisional Patent Application No. 61/172,426, filed on Apr. 24, 2009. The above-noted Applications are incorporated by reference as if set forth fully herein.

FIELD OF THE INVENTION

The field of the invention generally relates to medical devices and methods of treating the sinus system of a mammal such as a human.

BACKGROUND

Interest continues to increase in the potential for site-specific drug delivery in the sinuses and sinus drainage pathways. Once such device is described in U.S. Pat. No. 7,419,497. In one embodiment, '497 teaches a balloon that is placed in situ, filled with a drug-containing material (e.g., a steroid cream), and left in place for an extended period of time (e.g., 2 weeks). The '497 balloon has weep holes which allow the drug-containing material to ooze out over time.

SUMMARY OF THE INVENTION

This invention is directed towards devices and methods of use relating to implanting a fluid-dispensing implant within the frontal sinus system of a human.

In some embodiments, the invention includes a method of delivering a fluid to the frontal sinus system of a mammal, the method comprising directing an implant into a frontal sinus system of the mammal. The implant can include at least one fluid reservoir, at least one anchoring structure, and at least one dispensing structure. The dispensing structure can be in fluid communication with the fluid reservoir. The implant can be positioned so that the anchoring structure is located within a frontal sinus cavity of the frontal sinus system and most or all of the dispensing structure is located within the frontal sinus drainage pathway. A fluid can be directed from the fluid reservoir through the dispensing structure, thereby delivering the fluid to the frontal sinus system of the mammal over a period of time of at least a day. In this way, at least a portion of the fluid enters the frontal sinus drainage pathway directly from the dispensing structure. In some embodiments, the entire dispensing structure is located within the frontal sinus drainage pathway so that all or substantially all of the fluid enters the frontal sinus drainage pathway directly from the dispensing structure.

In some embodiments, the fluid reservoir is an inflatable structure (e.g., a balloon) while in other embodiments the fluid reservoir is a rigid container. The dispensing structure can be, for example, a plurality of holes disposed within an outer surface of the inflatable structure and/or disposed within an outer surface of a tube connected to the fluid reservoir. The holes can be in fluid communication with an interior portion of the balloon. In some embodiments, the fluid reservoir is an inflatable structure and can be expanded by directing the fluid to an interior portion of the inflatable structure. In some embodiments, most or all of the fluid reservoir is positioned within the frontal sinus drainage pathway, while in other embodiments most or all of the fluid reservoir is positioned within the frontal sinus cavity.

In some embodiments, the invention includes a method of delivering a fluid to the frontal sinus system of a mammal. The method includes directing an implant into a frontal sinus system of a mammal, the implant including at least one inflatable structure, one anchoring structure, and one dispensing structure. The anchoring structure is directed into a frontal sinus cavity of the frontal sinus system. The dispensing structure is directed into a portion of a frontal sinus drainage pathway in fluid communication with the sinus cavity. The anchoring structure is secured within a frontal sinus cavity of the frontal sinus system. The inflatable structure is expanded by directing a fluid into the inflatable structure. The fluid is dispensed directly into the frontal sinus drainage pathway from the dispensing structure, the fluid being delivered over a period of time of at least a day (e.g., one day, two days, three days, a week, two weeks, a month, or several months). The dispensing structure can be a plurality of holes in the inflatable structure or a plurality of holes that are situated on the outer surface of a hollow lumen that is in fluid communication with the inflatable structure. In some embodiments, the inflatable structure is positioned within the frontal sinus cavity while in other embodiments it is positioned within the frontal sinus drainage pathway.

In some embodiments, to ease insertion into the anatomy, the anchoring structure, the inflatable structure, or both are secured in a hollow lumen when the implant is directed into the frontal sinus system. In some embodiments, the inflatable structure is a non-cylindrical balloon (e.g., a lobed balloon).

The fluid used in the method can include a pharmaceutical agent. The inflatable structure can be "recharged" by directing another portion of fluid into the inflatable structure after the initial fluid-dispensing interval period of time.

In further embodiments, the method includes directing an implant into a frontal sinus system of a mammal, the implant including at least one inflatable structure and one anchoring structure, the anchoring structure being secured to a distal portion of the implant and the inflatable structure being positioned proximal relative to the anchoring structure. The anchoring structure can be directed into a frontal sinus cavity of the frontal sinus system and the inflatable structure can be directed into a portion of the frontal sinus drainage pathway. A fluid can be directed into the inflatable structure, the fluid comprising a drug. The fluid is directed into the frontal sinus drainage pathway from holes in the outer surface of the inflatable structure, the fluid being delivered over a period of time of at least a day (e.g., one day, two days, three days, a week, two weeks, a month, or several months).

BRIEF DESCRIPTION OF THE DRAWINGS

FIG. 1 illustrates a schematic representation of an embodiment of the present invention that includes a distal portion of a catheter.

FIG. 2 illustrates a schematic representation of an embodiment of the present invention that includes a catheter.

FIG. 4 illustrates a schematic representation of an embodiment of the present invention that includes a distal portion of a catheter.

FIG. 5 illustrates a schematic representation of an embodiment of the present invention that includes a catheter.

DETAILED DESCRIPTION

Historically, there has been some amount of confusion in the anatomical nomenclature of the human sinus system because the sinus system is fairly complicated and can vary between individuals. The frontal sinus system in particular has a complex and variable drainage system, compared to the other paranasal sinuses. As used herein, the "frontal sinus system" includes the frontal sinus cavities and the frontal sinus drainage pathway (further described below).

Figure 8:
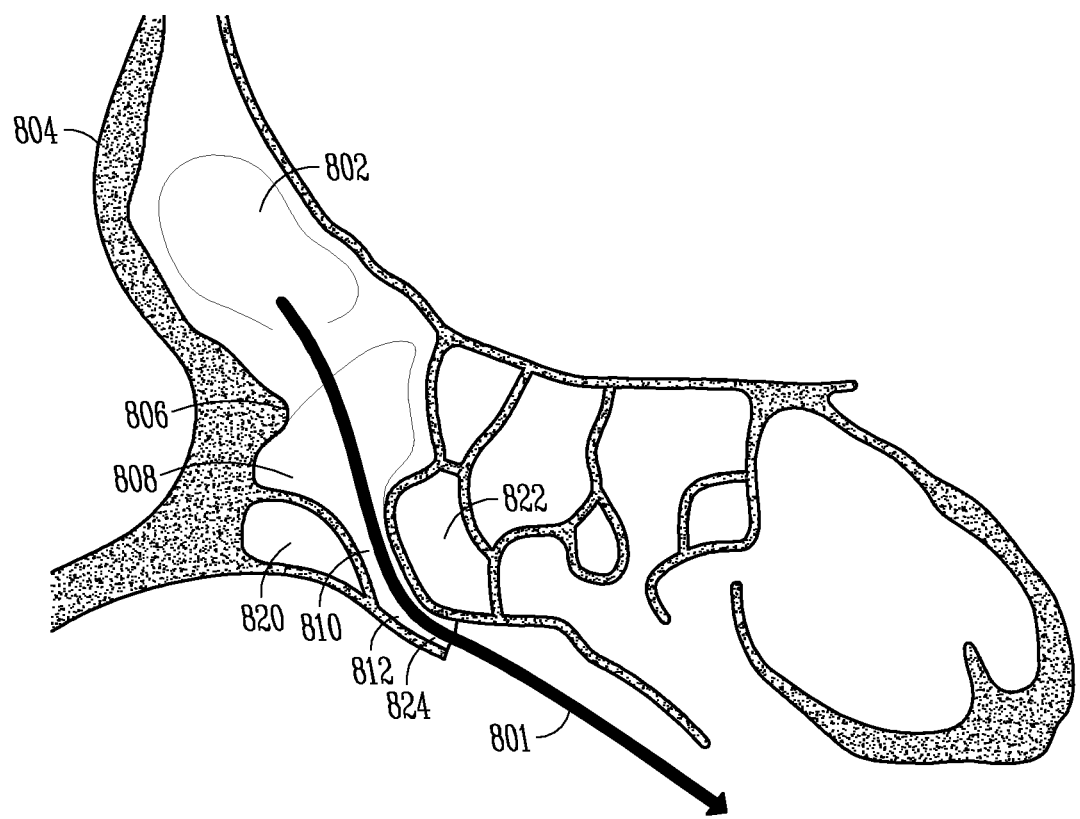
FIG. 8 illustrates a schematic representation of a side view of one half of a typical frontal sinus system.

FIG. 8 illustrates a schematic representation of a side view of one half of a typical frontal sinus system. The general drainage flow pathway of the frontal sinus system is illustrated as arrow 801, which extends from the frontal sinus cavity 802 and drains into the nasal cavity. The frontal sinus cavity 802 is located behind the supercilliary arch 804. The cavity 802 typically narrows down to an inferior margin called the frontal ostium 806 which extends between the anterior and posterior walls of the frontal sinus 802. The frontal ostium 806 is demarcated by a shaped ridge of bone on the anterior wall of the sinus and is oriented nearly perpendicular to the posterior wall of the sinus.

The frontal sinus drainage pathway has a superior and inferior component indicated generally as 808 and 810, respectively. The superior component 808 is formed by the union of adjacent air spaces at the anterioinferior portion of the frontal bone and the anteriosuperior portion of the ethmoid bone, its upper border being the frontal ostium 806. The superior component 808 is in direct fluid communication with the inferior component 810. The inferior component 810 is a narrow passageway typically formed by ethmoid air cells, such as the agger nasi 820 and ethmoid bulla 822, and may further include the ethmoid infundibulum 824. When the anterior portion of the uncinate process 812 extends superiorly to attach to the skull base (not illustrated), the inferior compartment 810 includes the ethmoid infundibulum 824. When the anterior portion of the uncinate process 812 extends superiorly to attach to the skull base (not illustrated), the inferior compartment 810 includes the ethmoid infundibulum 824. When the anterior portion of the uncinate process 812 is attached to the lamina papyracea instead of the skull base (not illustrated), the inferior compartment 810 is then the middle meatus (not illustrated). As used herein, the "frontal sinus drainage pathway" or "frontal sinus drainage system" is defined as the combination of the superior component 808 and inferior component 810 and is demarcated by the frontal ostium 806 and inferiorly by the floor of the inferior component.

FIGS. 1 and 2 illustrate an embodiment of the present invention, which includes the distal portion 100 of catheter 126. The Balloon catheter includes a fluid reservoir in the form of membrane or balloon portion 102. Distal portion 100 includes an anchoring structure in the form of two retention members or wings 104 attached or extending distally from distal tip 116 of balloon portion 102. Because wings 104 are positioned distally from balloon portion 102, distal portion 100 can be positioned in the drainage pathway of a frontal sinus (rather than in the sinus cavity itself) while wings 104 are extended or deployed within the sinus cavity to maintain the position of the implant.

Balloon portion 102 includes a dispensing structure in the form of a series of transport passage or ports 106 that allow a fluid material (e.g., a drug-containing material or agent, such as an anti-scarring or tissue proliferation agent) to weep out of balloon portion 102 once implanted into a sinus drainage pathway. Most or all of balloon portion 102 is placed within the drainage pathway itself, which allows the drug to be more effectively delivered to this region as compared to a device that releases a drug-containing material within the sinus cavity. For example, distal portion 100 can be placed within a frontal drainage pathway to prevent scarring or closure of the frontal recess via a combination of pharmaceutical activity from the wept material as well as the physical blockage represented by the presence of balloon portion 102 itself.

Distal portion 100 includes valve member 108 which acts as a one-way valve to allow for filling of balloon portion 102 with a material along path 110 which flows through catheter shaft 112 and out into an interior of balloon portion 102 via port 114. Valve member 108 is preferably circular, with a hole in the center. Under pressure, the fluid material deflects the valve member 108 and passes distally or antegrade into the body of balloon portion 102. After pressure is released, valve member 108 resumes its relaxed shape and closes off the hole in its center, thereby preventing retrograde flow through shaft 112. The fluid material weeps out of balloon portion 102 along or parallel to paths 118 via ports 106 to dispense the material in situ.

FIG. 2 illustrates most of the length of catheter 126. Sheath 120 is disposed along a length of shaft 112 of catheter 126. In use, sheath 120 is initially positioned to cover collapsed balloon portion 102a and all or most of retention wings 104. Once positioned in a desired location (e.g., with balloon portion 124 and wings 104 in the frontal drainage pathway and frontal sinus, respectively), sheath 120 is pulled back along shaft 112 to allow wings 104 to expand radially outward relative to the central axis of shaft 112 and sufficiently enough to remove balloon portion 102 from the lumen of sheath 120. In this manner, the outer diameter of the anchoring structure (e.g., retention wings 104) is expanded within the frontal sinus cavity as illustrated, for instance, in FIG. 3. Then balloon portion 102 is inflated with air or a fluid (e.g., a drug-containing fluid) to form inflated balloon portion 102b. In some embodiments, insertion of catheter 126 and positioning of balloon portion 102 is facilitated by a guide catheter (not illustrated). In other embodiments, catheter 126 is inserted by direct placement, preferably under endoscopic visualization. In yet further embodiments, the catheter shaft or portions thereof are curved to facilitate placement within the human anatomy.

Figure 3:
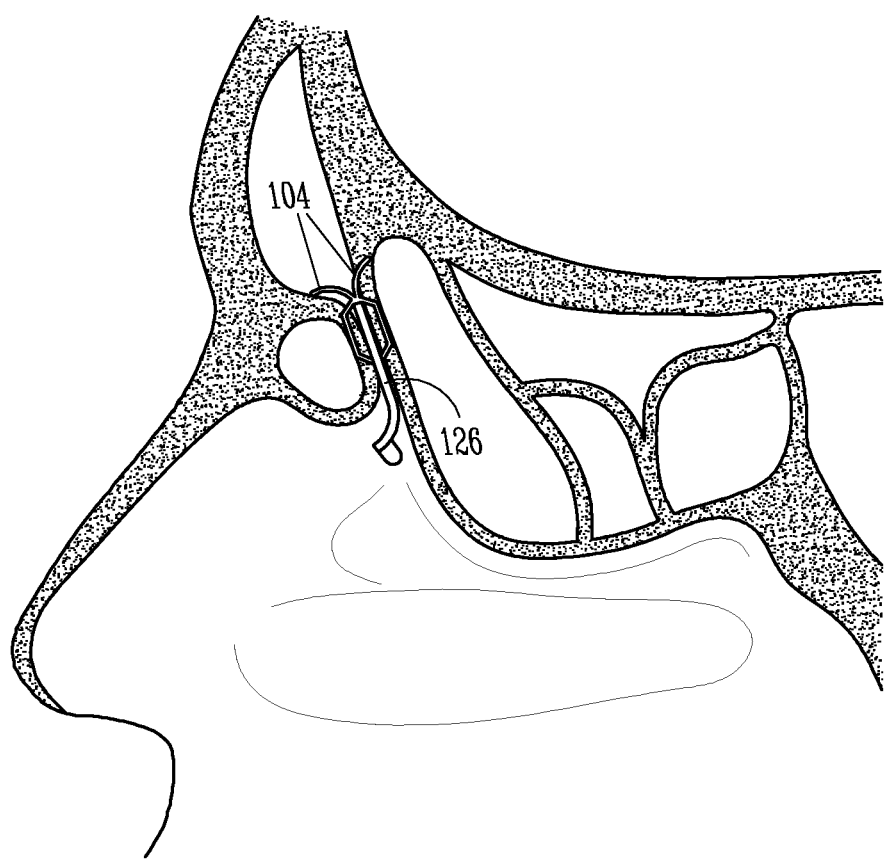
FIG. 3 illustrates a portion of the catheter of FIGS. 1 and 2 installed within the frontal sinus and frontal sinus drainage pathway.

FIG. 3 illustrates a portion of catheter 126 installed within the frontal sinus and frontal drainage pathway. Specifically, wings 104 have been deployed within the frontal sinus cavity and inflated balloon portion 102b is located within the frontal drainage pathway. Once positioned and filled, most of shaft 112 is cut away from inflated balloon portion 102b, leaving behind portion of shaft 126. The proximal cut end of portion of shaft 126 can be further secured to the nasal mucosa with a suture or other suitable means. Alternatively, once shaft 112 is cut, the cut end of portion of shaft 126 can be directed or "tucked away" into the maxillary ostium or behind the uncinate process so as to be completely out of the breathing space of the nasal passages. After an appropriate amount of time (e.g., ~2 weeks in the case of delivering a steroid compound), the implanted portions of the device can be removed by gentle traction. The desired length of in situ time will be a function of the drug used, the amount of time it takes for the drug-containing material to weep out of the device, and/or surgeon preference.

FIGS. 4 and 5 illustrate another embodiment of the invention that includes catheter 400. Illustrated in FIG. 4, distal portion 402 of catheter 400 includes a fluid reservoir in the form of balloon portion 404 and an anchoring structure in the form of retention wings 406. Retention wings 406 are secured to the distal tip of core 408. Core 408 is slidably arranged within the lumen of shaft 410. Core 408 can move relative to shaft 410 along direction 412. In some embodiments, core 408 is frictionally engaged with some other portion of catheter 400 to provide an amount of resistance between the relative movement between core 408 and shaft 410. For example, in some embodiments, tip 414 of catheter 402 creates a frictional engagement with core 408. Alternatively, or in addition, valve member 416 can create a frictional engagement with core 408.

FIG. 5 illustrates a part of the deployment process for catheter 400. Prior to implantation, catheter 400 is arranged such that collapsed balloon portion 404a and retention wings 406 are located within a distal portion of sheath 418. Once directed to a desirable location within the frontal sinus system, sheath 418 is pulled proximally back relative to shaft 410 in a direction roughly parallel to arrow 412, thereby releasing retention wings 406 and removing collapsed balloon portion 404a from the lumen of sheath 418. Retention wings 406 can be deployed, for example, within a frontal sinus cavity.

Once retention wings 406 are deployed, core 408 can be moved relative to shaft 410 by applying a force sufficient to overcome the frictional engagement between core 408 and tip 414, valve member 416 and/or whatever other frictional engagement means are employed. In this manner, the relative distance between collapsed balloon 404a and retention wings 406 can be varied, thereby allowing a practitioner of this invention to place collapsed balloon 404a in a desirable location (e.g., within the frontal drainage pathway). Once positioned, collapsed balloon 404a is inflated or filled with a fluid material (e.g., a drug-containing material) to form inflated balloon 404b. After inflation, shaft 410 can be cut away and, optionally, whatever portion of the shaft that is not cut away from inflated balloon 404b can be secured to the nasal mucosa.

Figure 6:
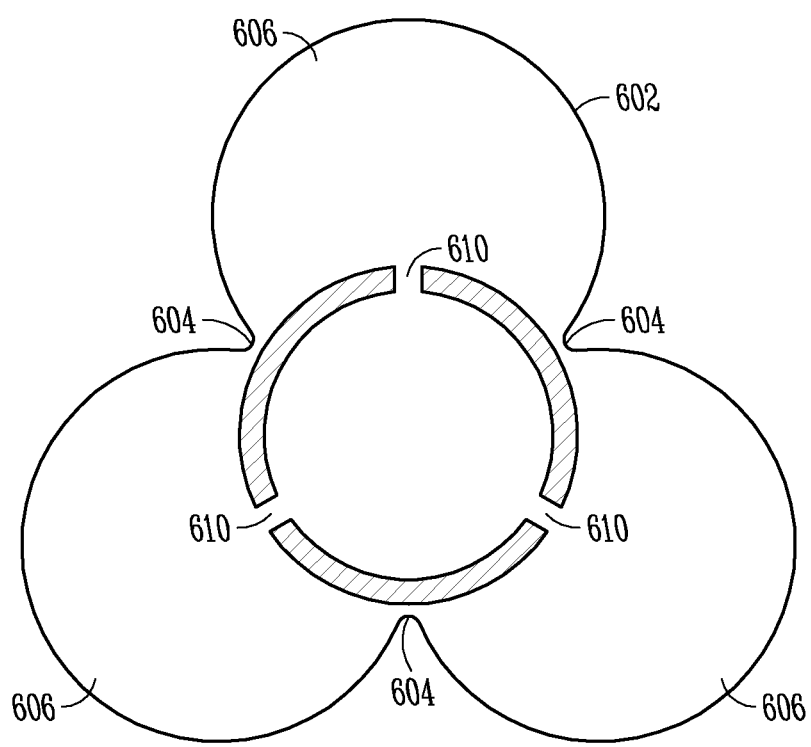
FIG. 6 illustrates a schematic representation of an embodiment of the present invention that includes a lobed balloon.

In some embodiments, the balloon portion is made to take some form of non-cylindrical shape when inflated with the fluid material. FIG. 6 illustrates one such embodiment where balloon 602 has, when inflated, a series of three "lobes" 606. Each lobe 606 is formed between two of points 604 which indicate places where the balloon membrane is attached or secured to shaft 608. When the fluid medium is directed into the balloon 602, it inflates and the three lobes 606 form a clover-like shape. A lobed-shaped balloon can be beneficial in that it will be less likely to obstruct the entire natural drainage pathway of a frontal sinus. While FIG. 6 illustrates an embodiment having three lobes, other embodiments of this invention includes balloons with 2, 4, or more than 4 lobes. A lobed-shaped balloon may be incorporated into any of the other embodiments described herein.

Figure 7:
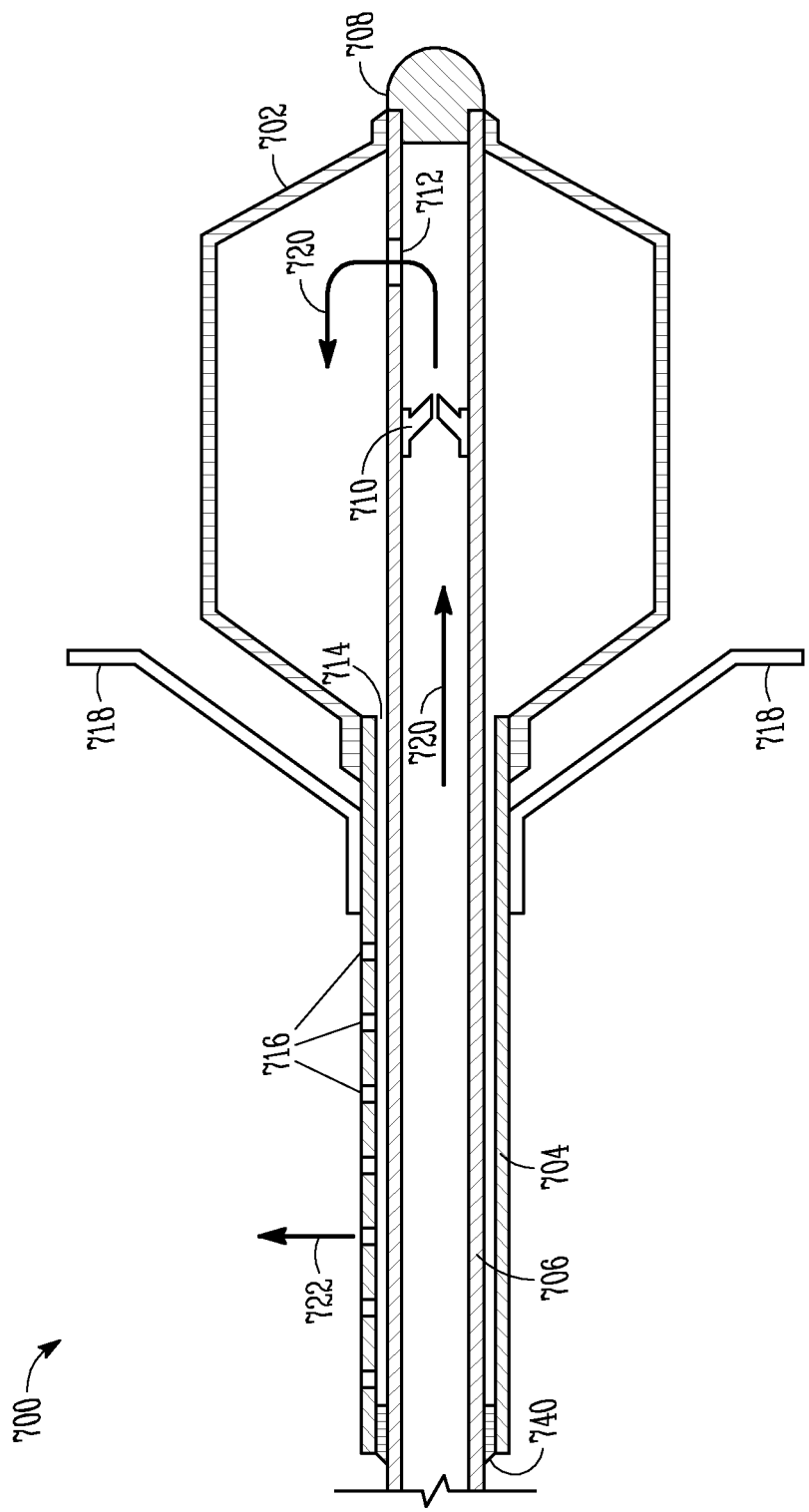
FIG. 7 illustrates a schematic representation of an embodiment of the present invention that includes a distal portion of a catheter.

In further embodiments of the invention, the dispensing structure takes the form of transport passages or ports, through which a drug-containing fluid can weep or otherwise be dispensed into the anatomy, that are located in a portion of the shaft. FIG. 7 illustrates one such embodiment.

Distal portion of catheter 700 includes a fluid reservoir structure in the form of balloon portion 702 attached to the distal end of a hollow shaft forming outer tube 704. Inner tube 706 is disposed within the lumen of outer tube 704. Inner tube 706 extends through outer tube 704 and balloon portion 702.

Cap 708 is disposed on the distal end of inner tube 706. Valve member 710 is disposed within the lumen of inner tube 706 and includes flow port 712. The lumen of inner tube 706 is in fluid communication with the interior of balloon portion 702 via port 712. The diameters of at least a portion of the distal ends of inner and outer tubes 706, 704 are dissimilar such that there is a small space or gap 714 therebetween. The distal end portion of outer tube 704 includes a dispensing structure in the form of a series of flow ports 716 in fluid communication with gap 714, interior of balloon portion 702 and the lumen of inner tube 706. An anchoring structure in the form of retention wings 718 are attached or secured to outer tube 704 at a location proximal relative to balloon portion 702. Sealing means 740 (e.g., a rubber washer or other plug) is positioned within gap 714 between inner and outer tubes 706, 704.

The embodiment illustrated in FIG. 7 can be implanted much the same way as the other embodiments illustrated herein, one of the main differences being that both balloon portion 702 and retention wings 718 can be placed within the frontal sinus cavity while a portion of inner and outer tubes 706, 704 extend down into the frontal sinus drainage pathway. Flow ports 716 in outer tube 704 will discharge or weep the fluid material directly into the drainage pathway while in the sinus cavity i) retention wings 718 secure the implant and ii) balloon portion 702 stores a supply of the fluid material. In this way, balloon portion 702 can be larger and store more fluid material relative to an embodiment where the balloon portion is positioned within the drainage pathway.

The embodiment described in FIG. 7 can be implanted using a sheath, similar to what was described above. Specifically, some or all of distal portion 700 can be contained within the lumen of a sheath, with un-deployed retention wings 718 and collapsed balloon portion 702 folded to a profile having a relatively small diameter. When directed to the desired position, the sheath can be slid proximally relative to outer and inner tube 704, 706, thereby allowing retention wings 718 to extend radially outward and, if the sheath contained balloon portion 702, and removing balloon portion 702 from the lumen of the sheath. Once distal portion 700 is in the desired location and the sheath (not illustrated in FIG. 7) has been slid back to release balloon portion 702 and retention wings 718, a fluid material (e.g., a drug-containing material) is directed up the lumen of inner tube 706 along direction 720, through valve member 710, and into the interior portion of balloon portion 702, thereby inflating balloon portion 702. Inner tube 706 is cut at a position (e.g., a position proximal relative to sealing means 720) that results in the desired length of its distal portion within the drainage pathway. In situ, fluid material flows from the interior of balloon portion 702 down through gap 714 and out ports 716 along direction 722.

In some embodiments, the balloon portion of the implant can be "recharged" one or more times with additional fluid material by, for example, delivering a fresh supply of the same or different fluid to the balloon portion with a syringe and needle. In this way, the invention can be used to administer a fluid to the sinus drainage pathway for a longer period of time.

Various modifications of the devices and methods described herein can be contemplated by those of skill in the art and are within the scope of this invention. Various specific dimensions and materials of the components of the device embodiments contemplated by those of skill in the art are also within the scope of the invention.

What is claimed is:

1. A method of delivering a fluid to the frontal sinus system of a mammal, the method comprising:
    directing an implant into a frontal sinus system of the mammal, the implant including at least one fluid reservoir, at least one anchoring structure, and at least one dispensing structure, wherein the dispensing structure is in fluid communication with the fluid reservoir, wherein the fluid reservoir is an inflatable structure, wherein the at least one anchoring structure is distal of a distalmost end of the at least one fluid reservoir;
    positioning the implant so that (i) the anchoring structure is located within a frontal sinus cavity of the frontal sinus system, (ii) an entirety of the dispensing structure is located within a frontal sinus drainage pathway, and (iii) an entirety of the fluid reservoir is located within the frontal sinus drainage pathway;
    expanding an outer diameter of the anchoring structure within the frontal sinus cavity;
    after expanding the outer diameter of the anchoring structure, inflating the fluid reservoir; and
    while the entirety of the dispensing structure and the entirety of the fluid reservoir are located within the frontal sinus drainage pathway, directing a fluid from the fluid reservoir through the dispensing structure, thereby delivering the fluid directly to the frontal sinus drainage pathway of the mammal over a period of time of at least a day.

2. The method of claim 1, wherein the inflatable structure is a balloon, the dispensing structure is a plurality of holes disposed within an outer surface of the balloon, and the holes are in fluid communication with an interior portion of the balloon.

3. The method of claim 1, wherein the inflatable structure is a balloon, the dispensing structure is a plurality of holes disposed within an outer surface of a tube connected to the balloon, and the holes are in fluid communication with an interior portion of the balloon.

4. The method of claim 1, further including expanding the inflatable structure by directing the fluid to an interior portion of the inflatable structure.

5. The method of claim 4, wherein the inflatable structure is positioned within the frontal sinus drainage pathway.

6. The method of claim 4, wherein the inflatable structure is not cylindrical when expanded.

7. The method of claim 6, wherein the inflatable structure is a lobed balloon.

8. The method of claim 1, wherein the anchoring structure includes two or more retention wings and expanding the outer diameter includes directing the two or more retention wings radially outward relative to a major axis of the implant.

9. The method of claim 1, wherein the fluid comprise a pharmaceutical agent.

10. The method of claim 1, wherein the anchoring structure is secured in a hollow lumen when the implant is directed into the frontal sinus system.

11. The method of claim 10, wherein the inflatable structure is secured in the hollow lumen when the implant is directed into the frontal sinus system.

12. The method of claim 1, further including directing a fluid into the fluid reservoir after the period of time of at least a day.

13. The method of claim 1, wherein the fluid is directed through a one-way valve member prior to being directed into the inflatable structure.

14. The method of claim 1, positioning the implant includes adjusting a relative distance between the fluid reservoir and the anchoring structure.

15. The method of claim 1, wherein the implant comprises a cap coupled to the distalmost end of the at least one fluid reservoir, and wherein the at least one anchoring structure is coupled to the cap.

16. The method of claim 1, wherein the at least one fluid reservoir is coupled to a catheter shaft, and wherein the method further comprises:
    after expanding an outer diameter of the anchoring structure within the frontal sinus cavity, cutting the catheter shaft; and
    removing a portion of the catheter shaft while retaining the at least one fluid reservoir in the frontal sinus drainage pathway.

17. The method of claim 1, wherein directing a fluid from the at least one fluid reservoir through the dispensing structure comprises weeping the fluid from the at least one fluid reservoir.

* * * * *